US011376425B2

(12) United States Patent
Finch et al.

(10) Patent No.: US 11,376,425 B2
(45) Date of Patent: Jul. 5, 2022

(54) CONTROLLING FUNCTIONS OF WEARABLE CARDIAC DEFIBRILLATION SYSTEM

(71) Applicant: West Affum Holdings Corp., Grand Cayman (KY)

(72) Inventors: David Peter Finch, Bothell, WA (US); Phillip Dewey Foshee, Jr., Woodinville, WA (US); Erick Michael Roane, Kirkland, WA (US); Laura Marie Gustavson, Redmond, WA (US); Kenneth F. Cowan, Kirkland, WA (US); Robert Reuben Buchanan, Bothell, WA (US); Daniel James Finney, Woodinville, WA (US); Jason W. Fouts, Bothell, WA (US); Gregory T Kavounas, Bellevue, WA (US)

(73) Assignee: West Affum Holdings Corp., Grand Cayman (KY)

( * ) Notice: Subject to any disclaimer, the term of this patent is extended or adjusted under 35 U.S.C. 154(b) by 287 days.

(21) Appl. No.: 16/678,727

(22) Filed: Nov. 8, 2019

(65) Prior Publication Data

US 2020/0147368 A1 May 14, 2020

Related U.S. Application Data

(63) Continuation of application No. 16/171,042, filed on Oct. 25, 2018, now Pat. No. 10,471,252, which is a (Continued)

(51) Int. Cl.
*A61N 1/08* (2006.01)
*A61N 1/39* (2006.01)
(Continued)

(52) U.S. Cl.
CPC ............... *A61N 1/08* (2013.01); *A61B 5/332* (2021.01); *A61B 5/6823* (2013.01);
(Continued)

(58) Field of Classification Search
CPC ...... A61N 1/08; A61N 1/3993; A61N 1/3925; A61B 5/332; A61B 5/6823; A61B 5/361;
(Continued)

(56) References Cited

U.S. PATENT DOCUMENTS 3,724,355 A 4/1973 Busch et al.
3,724,455 A 4/1973 Unger
(Continued)

FOREIGN PATENT DOCUMENTS

WO 9839061 A2 9/1998

OTHER PUBLICATIONS

Pagan-Carlo, et al., "Encircling Overlapping Multipulse Shock Waveforms for Transthoracic Defibrillation," JACC Journals, Dec. 1998, vol. 32 Issue 7, p. 2065-2071.
(Continued)

*Primary Examiner* — Mallika D Fairchild
(74) *Attorney, Agent, or Firm* — Spectrum IP Law Group LLC

(57) ABSTRACT

A Wearable Cardiac Defibrillator (WCD) system is configured to be worn by a patient who carries a mobile communication device. The mobile communication device has a user interface that is configured to enable the patient to enter wireless inputs. The WCD system includes a communication module that is configured to establish a local comlink with the mobile communication device. The WCD system also includes a tethered action unit that has a user interface configured to enable the patient to enter action inputs. The WCD system can perform some of its functions in response to the action inputs or to the wireless inputs. Since the
(Continued)

WEARABLE DEFIBRILLATOR SYSTEM
& MOBILE COMMUNICATION DEVICE wireless inputs can be provided from the mobile communication device instead of the action unit, the patient is less likely to attract attention when entering them, and thus exhibit better compliance.

20 Claims, 10 Drawing Sheets

Related U.S. Application Data continuation of application No. 14/684,274, filed on Apr. 10, 2015, now Pat. No. 10,155,110, and a continuation-in-part of application No. 14/454,517, filed on Aug. 7, 2014, now Pat. No. 9,079,045, which is a continuation of application No. 13/959,876, filed on Aug. 6, 2013, now Pat. No. 8,838,235.

(60) Provisional application No. 61/000,404, filed on May 19, 2014, provisional application No. 61/682,143, filed on Aug. 10, 2012, provisional application No. 61/706,697, filed on Sep. 27, 2012, provisional application No. 61/768,897, filed on Feb. 25, 2013.

(51) Int. Cl.
*A61B 5/00* (2006.01)
*A61B 5/332* (2021.01)
*A61B 5/0205* (2006.01)
*A61B 5/361* (2021.01)

(52) U.S. Cl.
CPC .......... *A61N 1/3993* (2013.01); *A61B 5/0024* (2013.01); *A61B 5/0205* (2013.01); *A61B 5/361* (2021.01); *A61B 5/6831* (2013.01); *A61B 5/6843* (2013.01); *A61N 1/3925* (2013.01)

(58) Field of Classification Search
CPC ... A61B 5/6831; A61B 5/6843; A61B 5/0024; A61B 5/0205
See application file for complete search history.

(56) References Cited

U.S. PATENT DOCUMENTS

| | | |
|---|---|---|
| 4,583,524 A | 4/1986 | Hutchins |
| 4,619,265 A | 10/1986 | Morgan et al. |
| 4,928,690 A | 5/1990 | Heilman et al. |
| 4,955,381 A | 9/1990 | Way et al. |
| 5,078,134 A | 1/1992 | Heilman et al. |
| 5,228,449 A | 7/1993 | Christ et al. |
| 5,348,008 A | 9/1994 | Bomn et al. |
| 5,353,793 A | 10/1994 | Bomn |
| RE34,800 E | 11/1994 | Hutchins |
| 5,394,892 A | 3/1995 | Kenny et al. |
| 5,405,362 A | 4/1995 | Kramer et al. |
| 5,474,574 A | 12/1995 | Payne et al. |
| 5,662,690 A | 9/1997 | Cole et al. |
| 5,782,878 A | 7/1998 | Morgan et al. |
| 5,792,204 A | 8/1998 | Snell |
| 5,902,249 A | 5/1999 | Lyster |
| 5,913,685 A | 6/1999 | Hutchins |
| 5,944,669 A | 8/1999 | Kaib |
| 6,047,203 A | 4/2000 | Sackner et al. |
| 6,065,154 A | 5/2000 | Hulings et al. |
| 6,108,197 A | 8/2000 | Janik |
| 6,148,233 A | 11/2000 | Owen et al. |
| 6,201,992 B1 | 3/2001 | Freeman |
| 6,263,238 B1 | 7/2001 | Brewer et al. |
| 6,287,328 B1 | 9/2001 | Snyder et al. |
| 6,292,687 B1* | 9/2001 | Lowell .................. A61B 5/002 600/515 |
| 6,304,780 B1 | 10/2001 | Owen et al. |
| 6,319,011 B1 | 11/2001 | Motti et al. |
| 6,334,070 B1 | 12/2001 | Nova et al. |
| 6,356,785 B1 | 3/2002 | Snyder et al. |
| 6,427,083 B1 | 7/2002 | Owen et al. |
| 6,437,083 B1 | 8/2002 | Brack et al. |
| 6,529,875 B1 | 3/2003 | Nakajima et al. |
| 6,546,285 B1 | 4/2003 | Owen et al. |
| 6,671,545 B2 | 12/2003 | Fincke |
| 6,681,003 B2 | 1/2004 | Linder et al. |
| 6,762,917 B1 | 7/2004 | Verbiest et al. |
| 7,065,401 B2 | 6/2006 | Worden |
| 7,277,752 B2 | 10/2007 | Matos |
| 7,559,902 B2 | 7/2009 | Ting et al. |
| 7,865,238 B2 | 1/2011 | Brink |
| 7,870,761 B2 | 1/2011 | Valentine et al. |
| 7,974,689 B2 | 7/2011 | Volpe et al. |
| 8,135,462 B2 | 3/2012 | Owen et al. |
| 8,140,154 B2 | 3/2012 | Donnelly et al. |
| 8,369,944 B2 | 2/2013 | Macho et al. |
| 8,548,557 B2 | 10/2013 | Garstka et al. |
| 8,615,295 B2 | 12/2013 | Savage et al. |
| 8,644,925 B2 | 2/2014 | Volpe et al. |
| 8,897,860 B2 | 11/2014 | Volpe et al. |
| 8,904,214 B2 | 12/2014 | Volpe et al. |
| 8,965,500 B2 | 2/2015 | Macho et al. |
| 9,008,801 B2 | 4/2015 | Kaib et al. |
| 9,089,685 B2 | 7/2015 | Sullivan et al. |
| 9,131,901 B2 | 9/2015 | Volpe et al. |
| 9,132,267 B2 | 9/2015 | Kaib |
| 9,408,548 B2 | 8/2016 | Volpe et al. |
| 9,454,219 B2 | 9/2016 | Volpe et al. |
| 9,592,403 B2 | 3/2017 | Sullivan |
| 2011/0022105 A9 | 1/2003 | Owen et al. |
| 2003/0158593 A1 | 8/2003 | Heilman et al. |
| 2005/0107833 A1 | 5/2005 | Freeman et al. |
| 2005/0107834 A1 | 5/2005 | Freeman et al. |
| 2007/0162090 A1* | 7/2007 | Penner ............... A61N 1/37235 607/60 |
| 2008/0312709 A1 | 12/2008 | Volpe et al. |
| 2009/0005827 A1 | 1/2009 | Weintraub et al. |
| 2010/0007413 A1 | 1/2010 | Herleikson et al. |
| 2010/0241181 A1 | 9/2010 | Savage et al. |
| 2010/0298899 A1 | 11/2010 | Donnelly et al. |
| 2011/0288604 A1 | 11/2011 | Kaib et al. |
| 2011/0288605 A1 | 11/2011 | Kaib et al. |
| 2012/0112903 A1* | 5/2012 | Kaib .................. A61B 5/14542 340/539.12 |
| 2012/0144551 A1 | 6/2012 | Guldalian |
| 2012/0150008 A1 | 6/2012 | Kaib et al. |
| 2012/0158075 A1 | 6/2012 | Kaib et al. |
| 2012/0265265 A1 | 10/2012 | Razavi et al. |
| 2012/0283794 A1 | 11/2012 | Kaib et al. |
| 2012/0293323 A1 | 11/2012 | Kaib et al. |
| 2012/0302860 A1 | 11/2012 | Volpe et al. |
| 2012/0310315 A1 | 12/2012 | Savage et al. |
| 2013/0085538 A1 | 4/2013 | Volpe et al. |
| 2013/0231711 A1 | 9/2013 | Kaib et al. |
| 2013/0245388 A1 | 9/2013 | Rafferty et al. |
| 2013/0274565 A1 | 10/2013 | Langer et al. |
| 2013/0317852 A1 | 11/2013 | Worrell et al. |
| 2013/0325078 A1 | 12/2013 | Whiting et al. |
| 2013/0337976 A1* | 12/2013 | Yanev ................ A61B 5/14532 482/8 |
| 2014/0025131 A1 | 1/2014 | Sullivan et al. |
| 2014/0070957 A1 | 3/2014 | Longinotti-Buitoni et al. |
| 2014/0163663 A1 | 6/2014 | Poddar et al. |
| 2014/0324112 A1 | 10/2014 | Macho et al. |
| 2014/0378812 A1 | 12/2014 | Saroka et al. |
| 2015/0039053 A1 | 2/2015 | Kaib et al. |
| 2015/0328472 A1 | 11/2015 | Sullivan et al. |
| 2016/0004831 A1 | 1/2016 | Carlson et al. |
| 2016/0082277 A1 | 3/2016 | Foshee, Jr. et al. |

OTHER PUBLICATIONS

Heartstart MRx and XL AED Algorithm—Application Note, Jul. 2001, Edition 2 Philips Healthcare, USA.

(56) References Cited

OTHER PUBLICATIONS

Klein, H. U., Goldenberg I., & Moss, A. J., Risk Stratification for Implantable Cardioverter Defibrillator Therapy: The Role of the Wearable Cardioverter-Defibrillator, Clinical update, European Heart Journal, May 31, 2013, pp. 1-14, doi:10.1093/eurheartj/eht167, European Society of Cardiology.

LIFECOR LifeVest System Model WCD 3100 Operator's Manual, 2006, PN 20B0040 Rev Fl, Zoll Lifecor Corporation, Pittsburgh, PA.

LifeVest Model 4000 Patient Manual, Zoll, 2009, PN 20B0047 Rev B.

The LifeVest Network/Patient Data Management System, Zoll, 2015, 20C0503 Rev A.

\* cited by examiner

*WEARABLE DEFIBRILLATOR SYSTEM & MOBILE COMMUNICATION DEVICE*

COMPONENTS OF EXTERNAL DEFIBRILLATOR

*REDUNDANT CONTROL OF SOME FUNCTIONS IN PREFERRED PRIVACY DOMAINS*

EXCLUSIVE CONTROL
OF SOME FUNCTIONS IN
PREFERRED PRIVACY DOMAINS

FIG. 7  *METHODS*

MUTUALLY EXCLUSIVE CONTROL OF SOME FUNCTIONS IN PREFERRED PRIVACY DOMAINS

METHODS

WCD SYSTEM WITH CARRIED COMPONENT

CONTROLLING FUNCTIONS OF WEARABLE CARDIAC DEFIBRILLATION SYSTEM

CROSS REFERENCE TO RELATED PATENT APPLICATIONS

This patent application claims priority from U.S. Provisional Patent Application Ser. No. 62/000,404, filed on May 19, 2014, the disclosure of which is hereby incorporated by reference.

This patent application is a Continuation-In-Part of co-pending U.S. patent application Ser. No. 14/454,517, filed on Aug. 7, 2014, which is a Continuation of U.S. patent application Ser. No. 13/959,876, filed Aug. 6, 2013, which claims the benefit of priority of U.S. Provisional Patent Application Ser. No. 61/768,897, filed on Feb. 25, 2013, and U.S. Provisional Patent Application Ser. No. 61/682,143, filed on Aug. 10, 2012, and U.S. Provisional Patent Application Ser. No. 61/706,697, filed on Sep. 27, 2012, the contents of all of which are incorporated herein by reference for all purposes.

BACKGROUND

When people suffer from some types of heart arrhythmias, the result may be that blood flow to various parts of the body is reduced. Some arrhythmias may even result in a Sudden Cardiac Arrest (SCA). SCA can lead to death very quickly, e.g. within 10 minutes, unless treated in the interim.

Some people have an increased risk of SCA. People at a higher risk include individuals who have had a heart attack, or a prior SCA episode. A frequent recommendation is for these people to receive an Implantable Cardioverter Defibrillator ("ICD"). The ICD is surgically implanted in the chest, and continuously monitors the person's electrocardiogram ("ECG"). If certain types of heart arrhythmias are detected, then the ICD delivers an electric shock through the heart.

After being identified as having an increased risk of an SCA, and before receiving an ICD, these people are sometimes given a wearable cardiac defibrillator ("WCD") system. A WCD system typically includes a harness, vest, or other garment that the patient is to wear. The WCD system includes a defibrillator and electrodes, coupled to the harness, vest, or other garment. When the patient wears the WCD system, the external electrodes may then make good electrical contact with the patient's skin, and therefore can help determine the patient's ECG. If a shockable heart arrhythmia is detected, then the defibrillator delivers the appropriate electric shock through the patient's body, and thus through the heart.

It is sometimes emotionally challenging to wear a WCD system. If others become aware of the WCD system, it draws unwanted attention to the patient. Others may become aware of it from how it protrudes from the patient's clothes. Even when not, some prior art WCD systems have a custom action unit with a user interface, through which a patient is expected to interact with the WCD system. The attention can be coupled with curiosity, since a WCD system is a rather unusual device. The attention can be embarrassing enough to the point where a patient might actually forego wearing their WCD system, thus diminishing compliance.

BRIEF SUMMARY

The present description gives instances of Wearable Cardiac Defibrillator (WCD) systems, storage media storing programs, and methods, the use of which may help overcome problems and limitations of the prior art.

In embodiments, a Wearable Cardiac Defibrillator (WCD) system is configured to be worn by a patient who carries a mobile communication device. The mobile communication device has a user interface that is configured to enable the patient to enter wireless inputs. The WCD system includes a communication module that is configured to establish a local comlink with the mobile communication device. The WCD system also includes a tethered action unit that has a user interface configured to enable the patient to enter action inputs. The WCD system can perform some of its functions in response to the action inputs or to the wireless inputs. Since the wireless inputs can be provided from the mobile communication device instead of the action unit, the patient is less likely to attract attention when entering the action inputs, and thus exhibit better compliance.

In embodiments, a Wearable Cardiac Defibrillator (WCD) system includes a support structure that is configured to be worn by the patient. A first electronics module is configured to be coupled to the support structure such that, when the support structure is worn by the patient, the first electronics module is substantially located at the lumbar region of the patient. This way, the support structure is less discernible to others, and the patient is less demotivated from wearing it.

These and other features and advantages of this description will become more readily apparent from the Detailed Description, which proceeds with reference to the associated drawings in which:

DETAILED DESCRIPTION

As has been mentioned, the present description is about Wearable Cardiac Defibrillator (WCD) systems, storage media storing programs, and methods. Embodiments are now described in more detail.

A Wearable Cardiac Defibrillator (WCD) system made according to embodiments has a number of components. These components can be provided separately as modules that can be interconnected, or can be combined with other components, etc.

A component of a WCD system can be a support structure, which is configured to be worn by the patient. The support structure can be any structure suitable for wearing, such as a harness, a vest, a half-vest—for example over the left side of the torso that positions electrodes on opposite sides of the heart, one or more belts that are configured to be worn horizontally or possibly vertically over a shoulder, another garment, and so on. The support structure can be implemented in a single component, or multiple components. For example, a support structure may have a top component resting on the shoulders, for ensuring that the defibrillation electrodes will be in the right place for defibrillating, and a bottom component resting on the hips, for carrying the bulk of the weight of the defibrillator. A single component embodiment could be with a belt around at least the torso. Other embodiments could use an adhesive structure or another way for attaching to the patient, without encircling any part of the body. There can be other examples.

Figure 1:
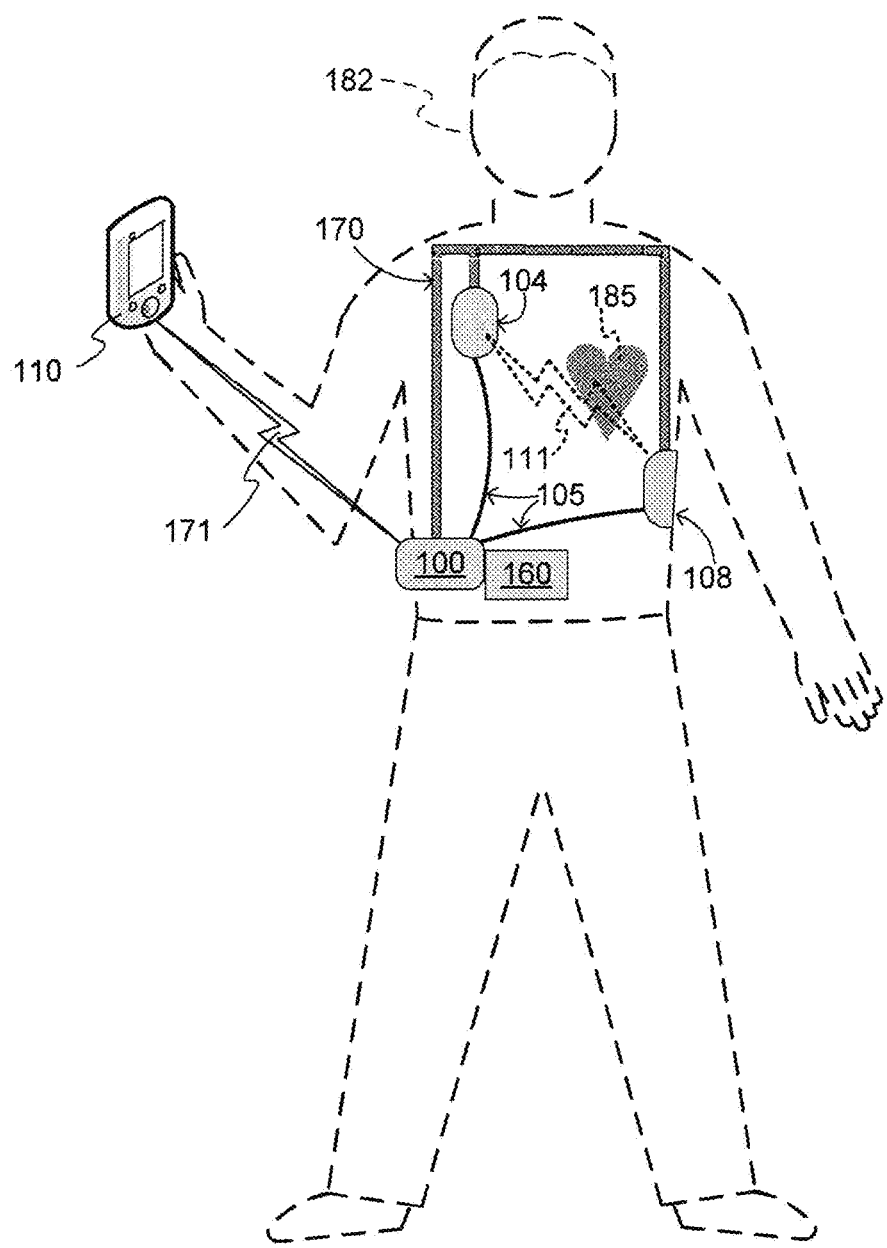
FIG. 1 is a diagram of components of a sample wearable cardiac defibrillator (WCD) system, made according to embodiments.

FIG. 1 depicts components of a WCD system made according to embodiments, as it might be worn by a person 182. A person such as person 182 may also be referred to as patient 182, wearer 182 since he or she wears the WCD system.

The components of the WCD system of FIG. 1 include a generic support structure 170 shown relative to the body of patient 182, and thus also relative to his or her heart 185. Structure 170 could be a harness, a vest, a half-vest, one or more belts, or a garment, etc., as per the above. Structure 170 could be implemented in a single component, or multiple components, and so on. Structure 170 is wearable by patient 182, but the manner of wearing it is not depicted, as structure 170 is depicted only generically in FIG. 1. Structure 170 can be designed to be worn under the clothes of patient 182, and can be shaped and sized to effectively remain hidden. This can be accomplished by thin materials, design principles that avoid often-exposed areas of a patient's anatomy (such as the neck, upper chest or lower arms), and/or providing an extensive range of sizes and/or adjustability.

A wearable cardiac defibrillator (WCD) system is configured to defibrillate a patient who is wearing it, by delivering electrical charge to the patient's body in the form of an electric shock delivered in one or more pulses. The components of the WCD system of FIG. 1 include a sample external defibrillator 100 made according to embodiments, and sample defibrillation electrodes 104, 108, which are coupled to external defibrillator 100 via electrode leads 105. Defibrillator 100 and defibrillation electrodes 104, 108 are coupled to support structure 170. As such, many of the individual components of defibrillator 100 can be therefore coupled to support structure 170. When defibrillation electrodes 104, 108 make good electrical contact with the body of patient 182, defibrillator 100 can administer, via electrodes 104, 108, a brief, strong electric pulse 111 through the body. Pulse 111, also known as a defibrillation shock or therapy shock, is intended to go through and restart heart 185, in an effort to save the life of patient 182. Pulse 111 can further include one or more pacing pulses, and so on. A prior art defibrillator typically decides whether to defibrillate or not based on an electrocardiogram ("ECG") signal of the patient. However, defibrillator 100 can defibrillate, or not defibrillate, also based on other inputs.

In the example of FIG. 1, defibrillator 100 includes additional individual components, as will be described in more detail later in this document. Briefly, these additional components include a power source that is configured to store an electrical charge, a discharge circuit, and one or more processors. In this example, the components also include a communication module that is integrated with the defibrillation unit in a single electronics module, although the communication module can be provided in an electronics module of the WCD system separately from that of the shown defibrillator 100.

In the example of FIG. 1, defibrillator 100 is shown in the front of the patient. In some embodiments, one or more components of a WCD system are preferably ergonomically designed to fit the lumbar region of the body. The lumbar region is sometimes referred to as the lower spine, or as an area of the back in its proximity. A component such as an electronics module may be discreetly worn on the body under a patient's clothes when placed in a lumbar pack/carrying case, or carried in a common accessory such as a purse or backpack—effectively hiding it in plain sight. Such an electronics module may include one or more components of the WCD system.

The components of the WCD system of FIG. 1 also include an action unit 160. Action unit 160 can be a device for patient 182 to exchange information with the WCD system. In particular, action unit 160 may have a user interface that is configured to enable patient 182 to read system messages and enter action inputs.

Action unit 160 can be configured to be coupled to support structure 170. In some embodiments, action unit 160 is integrated with the one or more processors in a single electronics module, for example the same electronics module that includes defibrillator 100. In some embodiments, action unit 160 is electrically coupled with the module of defibrillator 100 via a cable, which can be a permanent cable or a USB or Firewire connection.

For use, patient 182 may reach into their clothes to access action unit 160. In embodiments where a cable is used, patient 182 may bring action unit 160 to a comfortable position for reading the system messages and entering the action inputs. Accordingly, patient 182 can access and control various functions of the WCD system via action unit 160.

A problem with this arrangement, however, is that other people who can see action unit 160 might become curious, or even apprehensive. According to embodiments, some of the WCD system functions that can be controlled by access unit 160 can instead be controlled by a mobile communication device 110, redundantly or not.

In embodiments, then, patient 182 carries mobile communication device 110 on their person for typically much of the day. Patient 182 may carry device 110 in a pocket, in a special holder, or even wear it on their wrist. Patient 182 may use device 110 to communicate with the WCD system, which is why patient 182 may also be referred to as user 182. Mobile communication device 110 has a user interface that is configured to enable patient 182 to enter inputs that in this document are often called wireless inputs. Wireless communication links may be established and used in embodiments, for exchanging data, voice, etc. A wireless communication link is also sometimes referred to as "comlink".

A mobile communication device such as device 110 can be a custom-made device that is part of the WCD system. If made to look substantially like a common, commercially available mobile communication device, it might help preserve the privacy of patient 182 as to the fact that he or she is wearing a medical device, and thus also help preserve their dignity. In making such a custom-made device 110 appear like a commercially available mobile communication device, care should be taken to not use others' intellectual property rights without their permission.

Alternately, a mobile communication device such as device 110 can be a wireless telephone, a smartphone, a Personal Digital Assistant (PDA), a personal electronic device, a pager, a laptop computer, a tablet, an e-reader, and so on. It can have an app made according to embodiments, so as to perform various functions as described. In such embodiments, mobile communication device 110 can communicate with a wireless service provider network (not shown) via a remote comlink (not shown). For purposes of this document, a "remote comlink" means a wireless communication link established between devices that are at least 500 feet (150 m) away from each other, and typically farther, such as a cellular communication link. In such instances, the remote comlink can be used for a number of other functions, such as dialing an emergency number (e.g. 911 in the US), which may also be accessible via the mobile communication device directly. In addition, the location of the patient may be determined by GPS. If the WCD system and the mobile communication device have been paired and one of them knows that it is physically close to the other, GPS information may thus become known and communicated to EMS services. The mobile communication device may provide a redundant communication path for the data of the WCD system. This redundant communication path might be used as a secondary communication path for remote monitoring data if a primary, in-house internet path is not available for the WCD system to report. The remote comlink can also be used by a remote caregiver to provide patient 182 with troubleshooting assistance, motivational feedback, etc.

Mobile communication device 110 can thus be configured to establish a local comlink 171 with the communication module of the WCD system, which may be inside the same module as defibrillator 100. If mobile communication device 110 is indeed a wireless telephone or other independent standalone communication device, a local comlink may be established first pursuant to some authentication. Local comlink 171 may be established by the initiative of mobile communication device 110, the communication module, or both. For purposes of this document, a "local comlink" means a wireless communication link established between devices that are at most 50 feet (15 m) away from each other, and typically closer, such as when patient 182 is holding device 110. Local comlink 171 can be a wireless link. Data may be exchanged via local comlink 171, in either direction, or in both directions. In embodiments, local comlink 171 uses radio transmission technology that can be broadband and/or shortwave. Local comlink 171 may use Bluetooth technology, Wi-Fi technology, Zigbee or other suitable short-range wireless technology.

Figure 2:
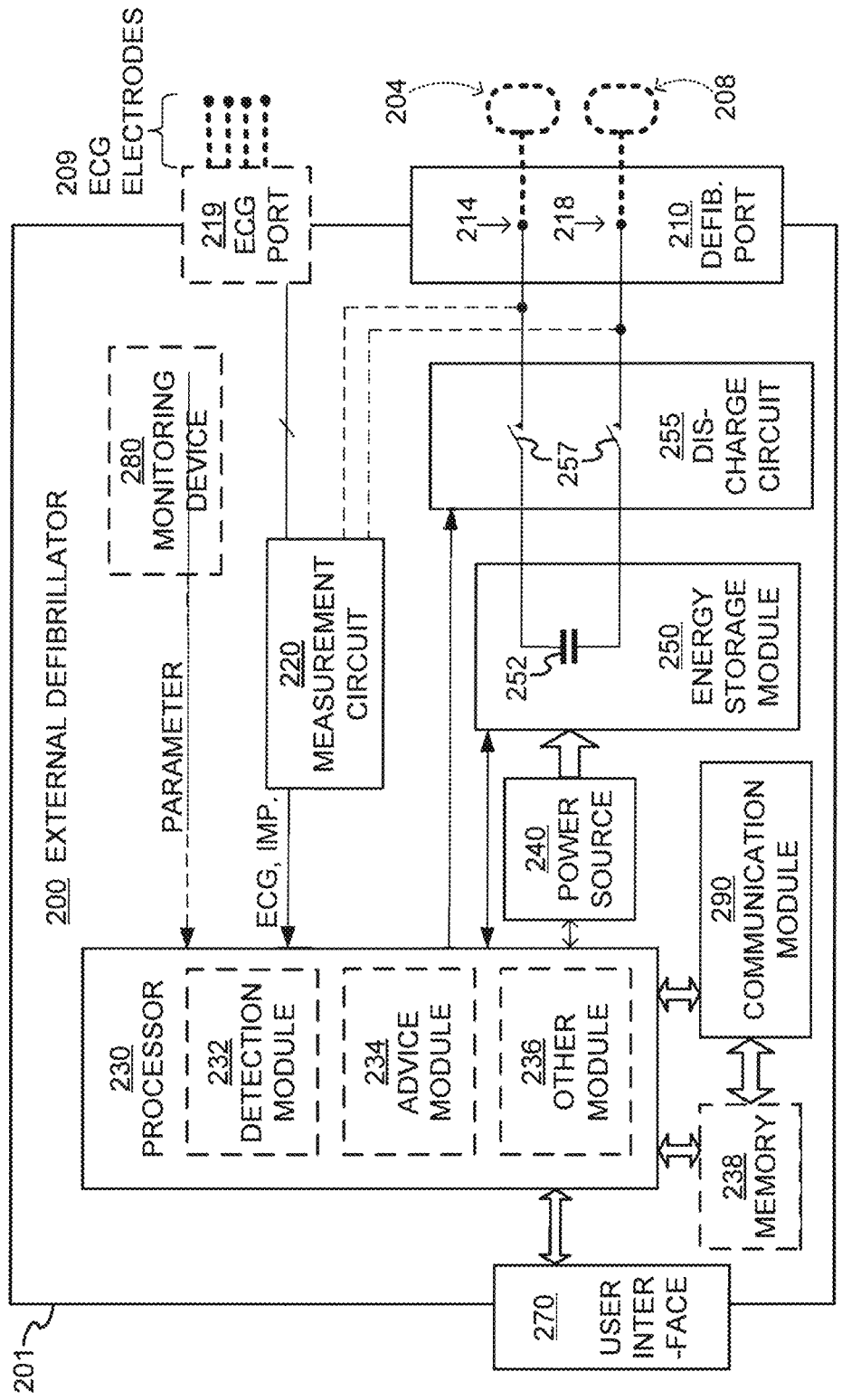
FIG. 2 is a diagram showing sample components of an external defibrillator, such as the one belonging in the system of FIG. 1, and which is made according to embodiments.

FIG. 2 is a diagram showing individual components of an external defibrillator 200, which is made according to embodiments. These individual components can be, for example, those included in the module that includes defibrillator 100 of FIG. 1. The components shown in FIG. 2 can be provided in a housing 201, which is also known as casing 201.

Defibrillator 200 is intended for a patient who would be wearing the WCD system, such as patient 182 of FIG. 1. Defibrillator 200 may further include a user interface 270, which can be the same as action unit 160. User interface 270 can thus be used by patient 182, or a bystander at a scene where the patient may experience SCA. The bystander may be a person familiar with patient 182, a stranger, a trained person, etc. In some scenarios the bystander may be a rescuer, etc.

User interface 270 can be made in a number of ways. User interface 270 may include output devices, which can be visual, audible or tactile, for communicating to a user. For example, an output device can be a light, or a screen to display what is detected and measured, and provide visual feedback to a rescuer for their resuscitation attempts, and so on. Another output device can be a speaker, which can be configured to issue voice prompts, etc. Sounds, images, vibrations, and anything that can be perceived by a user can also be called human perceptible indications. User interface 270 may also include input devices for receiving inputs from users. Such input devices may additionally include various controls, such as pushbuttons, keyboards, touchscreens, a microphone, and so on. An input device can be a cancel switch, which is sometimes called a "live-man" switch, an "I am OK" switch, a "divert therapy" switch, etc. In some embodiments, actuating the cancel switch can prevent the impending delivery of a shock.

The WCD system may optionally include a monitoring device 280. Device 280 can be configured to monitor at least one local parameter. A local parameter can be a physiological parameter of patient 182, or a parameter of the WCD system, or a parameter of the environment, as will be described later in this document. Patient physiological parameters include, for example, those physiological parameters that can be of any help in detecting by the wearable defibrillation system whether the patient is in need of a shock, plus optionally their medical history and/or event history. Examples of such parameters include the patient's ECG, blood oxygen level, blood flow, blood pressure, blood perfusion, pulsatile change in light transmission or reflection properties of perfused tissue, heart sounds, heart wall motion, breathing sounds and pulse. Accordingly, the monitoring device could include a perfusion sensor, a pulse oximeter, a Doppler device for detecting blood flow, a cuff for detecting blood pressure, an optical sensor, illumination detectors and perhaps sources for detecting color change in tissue, a motion sensor, a device that can detect heart wall movement, a sound sensor, a device with a microphone, an SpO2 sensor, and so on. Pulse detection is taught at least in Physio-Control's U.S. Pat. No. 8,135,462, which is hereby incorporated by reference in its entirety. In addition, a person skilled in the art may implement other ways of performing pulse detection.

Patient state parameters include recorded aspects of patient 182, such as motion, posture, whether they have spoken recently plus maybe also what they said, and so on, plus optionally the history of these parameters. Or, one of these monitoring devices could include a location sensor such as a Global Positioning System (GPS) location sensor. Such a sensor can detect the location, plus a speed can be detected as a rate of change of location over time. Many motion detectors output a motion signal that is indicative of the motion of the detector, and thus of the patient's body. Patient state parameters can be very helpful in narrowing down the determination of whether SCA is indeed taking place.

Defibrillator 200 typically includes a defibrillation port 210, such as a socket in housing 201. Defibrillation port 210 includes electrical nodes 214, 218. Leads of defibrillation electrodes 204, 208, such as leads 105 of FIG. 1, can be plugged in defibrillation port 210, so as to make electrical contact with nodes 214, 218, respectively. Electrodes 204, 208 can be electrodes 104, 108. Either way, defibrillation port 210 can be used for guiding, via electrodes, to the wearer the electrical charge that has been stored in energy storage module 250. The electric charge will be the shock for defibrillation, pacing, and so on.

Defibrillator 200 may optionally also have an ECG port 219 in housing 201, for plugging in sensing electrodes 209, which are also known as ECG electrodes and ECG leads. It is also possible that sensing electrodes 209 can be connected continuously to ECG port 219, instead. Sensing electrodes 209 can help sense an ECG signal, e.g. a 12-lead signal, or a signal from a different number of leads, especially if they make good electrical contact with the body of the patient. Sensing electrodes 209 can be attached to the inside of support structure 170 for making good electrical contact with the patient, similarly as defibrillation electrodes 204, 208.

Defibrillator 200 also includes a measurement circuit 220. Measurement circuit 220 receives physiological signals of the patient from ECG port 219, if provided. Even if defibrillator 200 lacks ECG port 219, measurement circuit 220 can obtain physiological signals through nodes 214, 218 instead, when defibrillation electrodes 204, 208 are attached to the patient. In these cases, the patient's ECG signal can be sensed as a voltage difference between electrodes 204, 208. Plus, impedance between electrodes 204, 208 and/or the connections of ECG port 219 can be sensed. Sensing the impedance can be useful for detecting, among other things, whether these electrodes 204, 208 and/or sensing electrodes 209 are not making good electrical contact with the patient's body. These patient physiological signals can be sensed, when available. Measurement circuit 220 can then render or generate information about them as physiological inputs, data, other signals, etc. More strictly speaking, the information rendered by measurement circuit 220 is output from it, but this information can be called an input because it is received by a subsequent device or functionality as an input.

A WCD system according to embodiments also includes one or more processors, of which defibrillator 200 shows only one processor 230. The one or more processors may be implemented in any number of ways. Such ways include, by way of example and not of limitation, digital and/or analog processors such as microprocessors and Digital Signal Processors (DSPs); controllers such as microcontrollers; software running in a machine; programmable circuits such as Field Programmable Gate Arrays (FPGAs), Field-Programmable Analog Arrays (FPAAs), Programmable Logic Devices (PLDs), Application Specific Integrated Circuits (ASICs), any combination of one or more of these, and so on.

The one or more processors may be configured to receive the action inputs that have been entered via the user interface of action unit 160, and the wireless inputs that have been entered via the user interface of mobile communication device 110. In addition, the one or more processors may be configured to perform various functions, for example by causing various components to operate in certain ways. In some embodiments, the performance of these functions can have aspects that are controlled by any received action inputs and wireless inputs.

A number of functions are possible according to embodiments, which the one or more processors can be configured to perform. Some of these functions are described later in this document. Of these functions, a first function can be to cause the patient to be defibrillated. This first function can be performed by controlling discharge circuit 255 to discharge the electrical charge stored in power source 240 through patient 182, while patient 182 is wearing support structure 170.

In the example of FIG. 2, for this first function processor 230 can be considered to have a number of modules. One such module can be a detection module 232. Detection module 232 can include a ventricular fibrillation ("VF") detector. The patient's sensed ECG from measurement circuit 220, which can be available as physiological inputs, data, or other signals, may be used by the VF detector to determine whether the patient is experiencing VF. Detecting VF is useful, because VF results in SCA. Detection module 232 can also include a ventricular tachycardia ("VT") detector, and so on.

Another such module in processor 230 can be an advice module 234, which generates advice for what to do. The advice can be based on outputs of detection module 232. There can be many types of advice according to embodiments. In some embodiments, the advice is a shock/no shock determination that processor 230 can make, for example via advice module 234. The shock/no shock determination can be made by executing a stored Shock Advisory Algorithm. A Shock Advisory Algorithm can make a shock/no shock determination from one or more of ECG signals that are captured according to embodiments, and determining whether a shock criterion is met. The determination can be made from a rhythm analysis of the captured ECG signal or otherwise.

In some embodiments, when the decision is to shock, an electrical charge is delivered to the patient. Delivering the electrical charge is also known as discharging. Shocking can be for defibrillation, pacing, and so on.

Processor 230 can include additional modules, such as other module 236, for other functions. In addition, if internal monitoring device 280 is indeed provided, it may be operated in part by processor 230, etc.

Defibrillator 200 optionally further includes a memory 238, which can work together with processor 230. Memory 238 may be implemented in any number of ways. Such ways include, by way of example and not of limitation, volatile memories, nonvolatile memories (NVM), read-only memories (ROM), random access memories (RAM), magnetic disk storage media, optical storage media, smart cards, flash memory devices, any combination of these, and so on. Memory 238 is thus a non-transitory storage medium. Memory 238, if provided, can include programs for processor 230, which processor 230 may be able to read and execute. More particularly, the programs can include sets of instructions in the form of code, which processor 230 may be able to execute upon reading. Executing is performed by physical manipulations of physical quantities, and may result in the functions, processes, actions and/or methods to be performed, and/or the processor to cause other devices or components or blocks to perform such functions, processes, actions and/or methods. The programs can be operational for the inherent needs of processor 230, and can also include protocols and ways that decisions can be made by advice module 234. In addition, memory 238 can store prompts for the user of user interface 270, if this user is a local rescuer. Moreover, memory 238 can store data. The data can include patient data, system data and environmental data, for example as learned by internal monitoring device 280 and outside monitoring device 180. The data can be stored in memory 238 before it is transmitted out of defibrillator 200, or stored there after it is received by defibrillator 200.

As mentioned previously, defibrillator 200 also includes a power source 240. To enable portability of defibrillator 200, power source 240 typically includes a battery. Such a battery is typically implemented as a battery pack, which can be rechargeable or not. Sometimes a combination is used of rechargeable and non-rechargeable battery packs. Other embodiments of power source 240 can include an AC power override, for where AC power will be available, an energy storage capacitor, and so on. In some embodiments, power source 240 is controlled by processor 230.

Defibrillator 200 additionally includes an energy storage module 250, which can thus be coupled to the support structure of the WCD system. Module 250 is where some electrical energy is stored in the form of an electrical charge, when preparing it for sudden discharge to administer a shock. Module 250 can be charged from power source 240 to the right amount of energy, as controlled by processor 230. In typical implementations, module 250 includes a capacitor 252, which can be a single capacitor or a system of capacitors, and so on. As described above, capacitor 252 can store the energy in the form of electrical charge, for delivering to the patient.

As mentioned previously, defibrillator 200 moreover includes a discharge circuit 255. When the decision is to shock, processor 230 can be configured to control discharge circuit 255 to discharge through the patient the electrical charge stored in energy storage module 250. When so controlled, circuit 255 can permit the energy stored in module 250 to be discharged to nodes 214, 218, and from there also to defibrillation electrodes 204, 208. Circuit 255 can include one or more switches 257. Switches 257 can be made in a number of ways, such as by an H-bridge, and so on. Circuit 255 can also be controlled via user interface 270.

As mentioned previously, defibrillator 200 includes a communication module 290, for establishing one or more wired or wireless communication links with other devices of other entities, such as a remote assistance center, Emergency Medical Services (EMS), device 110, and so on. In other embodiments, the communication module need not be in the same housing 201 as defibrillator 200. Module 290 may also include an antenna, portions of a processor, and other sub-components as may be deemed necessary by a person skilled in the art. This way, data and commands can be communicated via comlinks, such as patient data, event information, therapy attempted, CPR performance, system data, environmental data, and so on.

Defibrillator 200 can optionally include other components. Returning to FIG. 1, in embodiments, one or more of the components of the shown WCD system have been customized for patient 182. This customization may include a number of aspects. For instance, support structure 170 can be fitted to the body of patient 182. For another instance, baseline physiological parameters of patient 182 can be measured, such as the heart rate of patient 182 while resting, while walking, motion detector outputs while walking, etc. Such baseline physiological parameters can be used to customize the WCD system, in order to make its diagnoses more accurate, since bodies behave differently. For example, such parameters can be stored in a memory of the WCD system, and so on. A programming interface can be made according to embodiments, which receives such measured baseline physiological parameters. Such a programming interface may input automatically in the WCD system the baseline physiological parameters, along with other data.

It will be appreciated that embodiments give patient 182 the option to control the performance of a number of functions of the WCD system via mobile communication device 110, as opposed to action unit 160. Using device 110 will attract less attention in public places where others may be watching, than using action unit 160. In addition, using device 110 will be less distracting to people familiar with patient 182, and the fact that this patient needs to be attending to their WCD system. As such, patient 182 will have one less deterrent from exhibiting good compliance in actually wearing their WCD system daily.

Embodiments make various allocations as to which of action unit 160 and mobile communication device 110 can affect which functions of the processor(s) of the WCD system. In some embodiments there is redundancy, in that one or more functions can be accessed from either action unit 160 or mobile communication device 110, meaning aspects of the performance of these functions can be controlled either by received action inputs or by received wireless inputs. In some embodiments there is exclusivity, in that one or more functions can be accessed from either action unit 160 or mobile communication device 110, but not both. In some embodiments there is redundancy for some functions and exclusivity for others.

The allocations can be made by taking into account the context that functions may be performed in, in terms of criticality and afforded privacy. For example, there can be a preference that some initialization functions that are operated when patient 182 is initially fitted with the WCD system at the doctor's office be exclusively accessible and controllable by action unit 160, and not accessible by mobile communication device 110. For another example, there can be a preference that functions which patient 182 is expected to perform periodically be accessible from mobile communication device 110. For some of these choices it can be further considered that, in case of an emergency, action unit 160 may be more reliable if it does not need to be separately powered, or for a wireless network to be operating.

Examples are now described in more detail.

Figure 3:
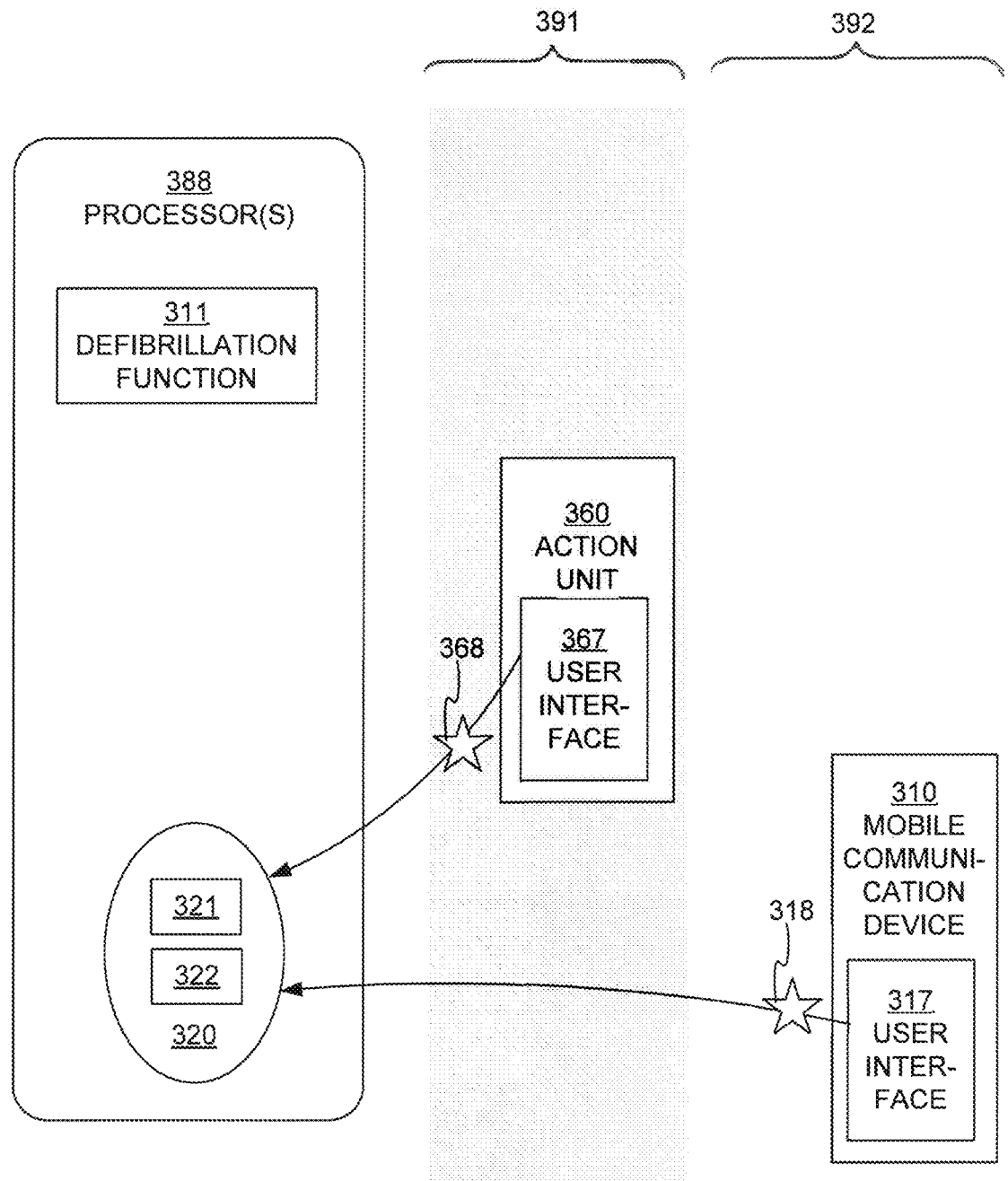
FIG. 3 is a diagram showing a sample allocation of access of functions according to embodiments.

FIG. 3 is a diagram showing a sample allocation of access of functions according to embodiments. A WCD system, which is not indicated separately, has one or more processors 388. Processor(s) 388 are configured to perform a defibrillation function 311, which is the function of causing the patient to be defibrillated as described above. Processor(s) 388 are further configured to perform at least one second function that is distinct from defibrillation function 311. In the example of FIG. 3, there is a set 320 of such possible additional second functions, namely functions 321, 322, although more are possible. Sample functions are described later in this document.

In FIG. 3, the WCD system also has an action unit 360, which can be as described for action unit 160. Action unit 360 has a user interface 367, which may receive action inputs 368 entered by the patient. When using the highly customized action unit 360, the patient may prefer to be in a more private context, which is indicated conceptually by showing customized action unit 360 in a gray domain 391. Action inputs 368 may affect the functions of set 320. More particularly, an aspect of the performance of one of the second functions in set 320 can be controlled by received action input 368.

In FIG. 3, the WCD system further cooperates with a mobile communication device 310, which can be as described for mobile communication device 110. Mobile communication device 310 has a user interface 317, which may receive wireless inputs 318 entered by the patient. When using mobile communication device 310, the patient may not mind being in a public space, which is indicated conceptually by showing mobile communication device 110 in a clear domain 392. Wireless inputs 318 may affect the functions of set 320. More particularly, an aspect of the performance of one of the second functions in set 320 can be controlled by received wireless input 318.

As can be seen, the functions of set 320 can be controlled either by action inputs 368 of action unit 360, or by wireless inputs 318 of mobile communication device 310. In another word, these functions can be controlled redundantly. As such, processor(s) 388 may receive an action input 368 and perform second function 321, in which an aspect of the performance of second function 321 can be controlled by received action input 368. Moreover, processor(s) 388 may receive wireless input 318 and subsequently perform again second function 321, in which the same aspect of the subsequent performance of second function 321 can be controlled by received wireless input 318.

Examples of functions are now described. It should be remembered that each of these functions may be designated for exclusive access by either action unit 360 or mobile communication device 310, or may be designed for redundant access by both. Additionally, one or more suitable interfaces can change these designations according to embodiments for an individual system, for example customized based on a particular patient. Moreover, a protocol and one or more suitable interfaces can be used to determine for any time or condition which of action unit 360 and mobile communication device 310 is accessing the second function in question.

In some embodiments, the second function includes causing a physiological parameter of the patient to be measured. This parameter can be the ECG, heart sounds, $CO_2$, etc. In some instances, the patient's cooperation is needed for this parameter to be measured. For example, the patient may need to become substantially motionless, or apply a measuring implement on his or her body, etc.

Figure 4:
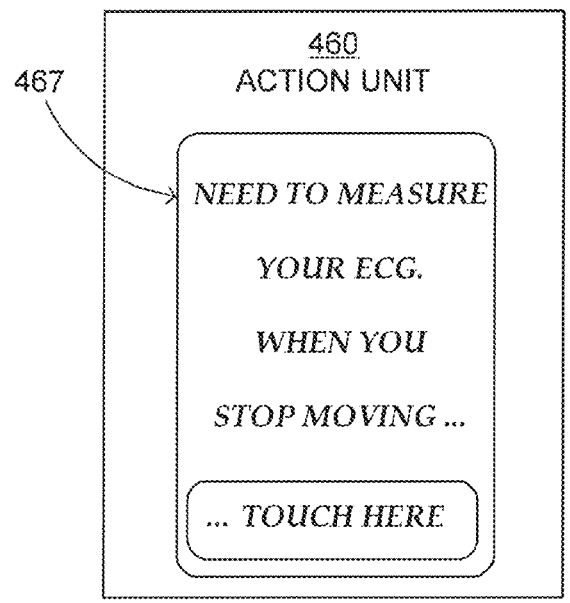
FIG. 4 is a diagram of a sample action unit with a user interface requesting an action input according to embodiments.

FIG. 4 is a diagram of an action unit 460, which can be as action unit 360. Action unit 460 has a user interface that includes a touchscreen 467. A message on touchscreen 467 requests an action input, namely for the patient to touch a specific place on touchscreen 467 after he or she has stopped moving.

In such embodiments, the controlled aspect of the performance of the second function, i.e. of the causing of the parameter to be measured, may include a time when the patient signifies that a condition for the measuring is optimized. In the example of FIG. 4, the time is defined by the moment the patient touches touchscreen 467 as requested. That time is when the patient thus signifies that a condition for the measuring is optimized, for example they have stopped moving as much as possible. If the second function includes causing to be measured a physiological parameter of the patient that is not the ECG, the patient could instead be signifying that he or she has applied the appropriate measuring implement on his or her body, etc.

In such embodiments, the controlled aspect of the performance of the second function, i.e. of the causing of the parameter to be measured, may include a time when the physiological parameter is measured. One example is again what was described with reference to FIG. 4. Another example can be to touch the screen while no therapy is indicated by a component of the WCD system, so as to "snapshot" a symptomatic episode, record more aspects of it, report it, and so on. Such a symptomatic episode could be further analyzed in addition with extra reporting by the patient to investigate for any further problems, or to add to their baseline of normal occurrences, and so on.

In embodiments where such second functions can be controlled redundantly, the messaging and exchange shown in FIG. 4 could have also occurred via an interface of a mobile communication device. After all, the WCD system may suspect activity, or a symptomatic episode may occur while the patient is in a context of domain 392, not 391, and reporting via the mobile communication device may be preferred.

In some embodiments, the second function includes settings of the WCD system, such as airplane mode selection, audio preferences such as non-safety-related audio preferences, etc. For example, the second function may include causing an auditory notification to be provided to the patient, and the controlled aspect of the performance of the second function may include a sound volume of the auditory notification. It will be further recognized that the sound volume may be set as an explicit setting, or be part of another setting that is of larger scope. An example is now described.

Figure 5:
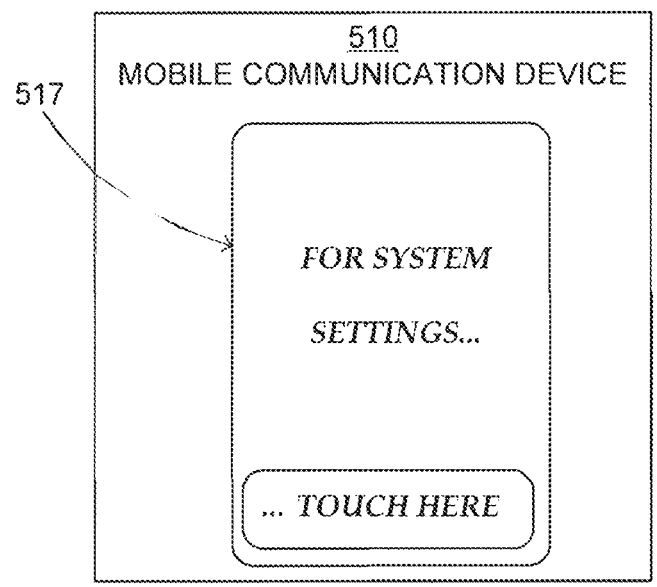
FIG. 5 is a diagram of a sample mobile communication device with a user interface requesting a wireless input according to embodiments.

FIG. 5 is a diagram of a sample mobile communication device 510, which can be as mobile communication device 110. Mobile communication device 510 has a user interface that includes a touchscreen 517. A message on touchscreen 517 requests a wireless input, namely for the patient to touch a specific place on touchscreen 517 for affecting settings of the WCD system. The settings could include a "return to default" setting, which may include a default sound volume setting. Again, in embodiments where such second functions can be controlled redundantly, the messaging and exchange shown in FIG. 5 could have also occurred via an interface of an action unit.

In some embodiments, the second function includes causing quality-of-life data to be received from the patient, which can be entered by the patient as one or more responses to a survey. In these embodiments, the controlled aspect of the performance of the second function can include a time that the quality-of-life data is received, which is controlled by when the patient enters the quality-of-life data.

In some embodiments, the second function includes causing condition data to be transmitted to a remote party that is designated as friendly to the patient. Indeed, as part of a support network to enhance patient compliance, such condition data can be shared with loved ones. If done via a mobile communication device that is also commercially available, the condition data can be transmitted via a secure application ("app"). The condition data can be physiological, and also mental or emotional, current or previous, and so on. In these embodiments, the controlled aspect of the performance of the second function may include a time that the condition data is transmitted.

In some embodiments, a "snooze" functionality is implemented, which can be activated prior to temporarily removing the WCD system. In such cases, the second function may include causing a certain operation to be performed, and the controlled aspect of the performance of the second function may include pausing the performance of the certain operation at a particular time. The particular time can be when the patient activates the snooze functionality. The certain operation may include transmitting data wirelessly, receiving data wirelessly, performing a diagnostic self-test, etc. As described above, the transmitted data can be WCD system data, environment data, patient data, etc.

Returning to FIG. 3, as mentioned previously, functions 321, 322 in set 320 are accessible redundantly. In addition to this, some additional functions may be accessible by only one of the action unit and the mobile communication device. For example, the one or more processors can be configured to further receive another one of the action inputs, and another one of the wireless inputs. The one or more processors can be configured to perform a third function that is distinct from the first function of defibrillation and the second functions. An aspect of the performance of the third function can be controlled by the received other action input, but not by the received other wireless input. Examples are now described.

Figure 6:
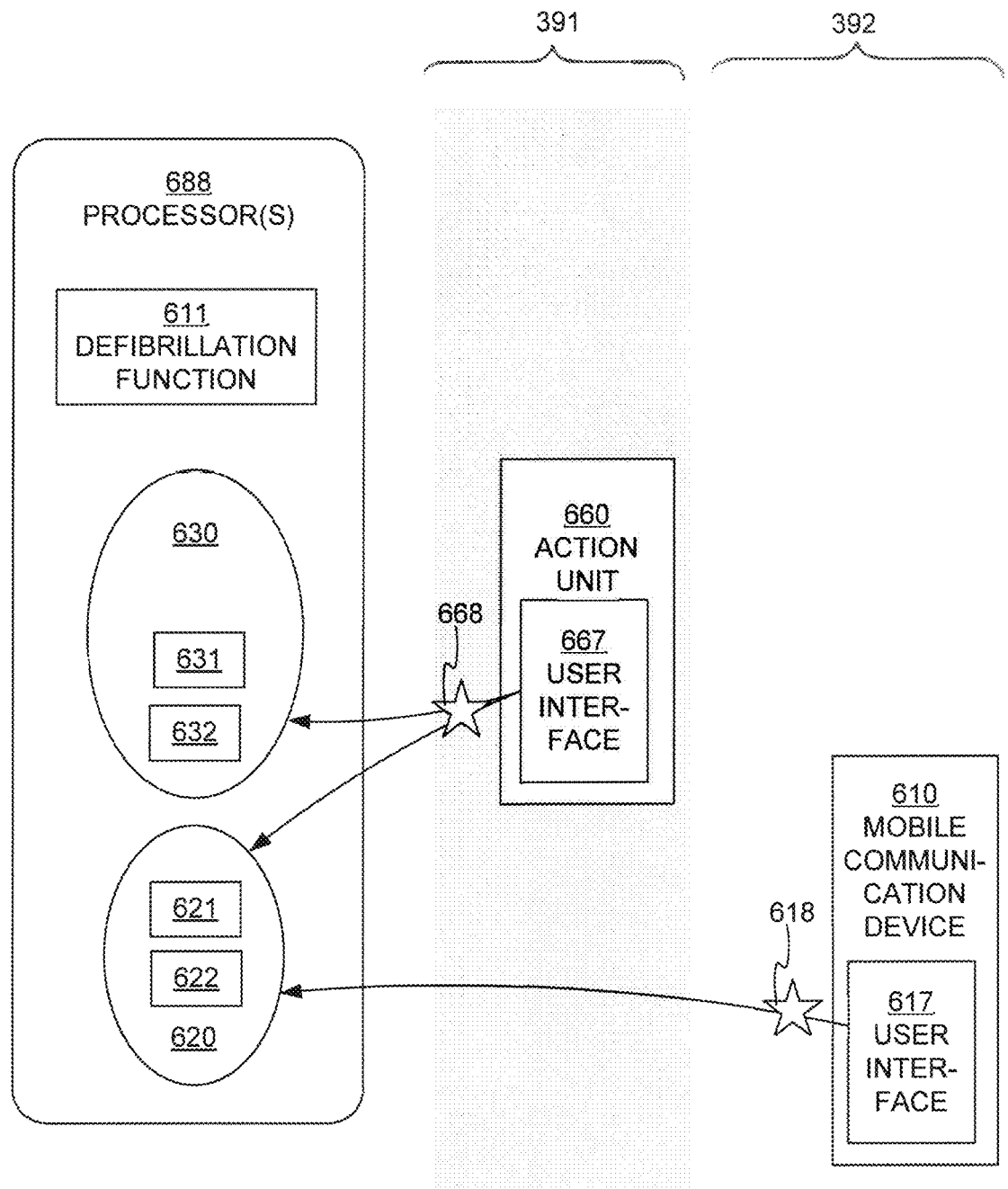
FIG. 6 is a diagram showing a sample allocation of access of functions according to embodiments.

FIG. 6 is a diagram showing a sample allocation of access of functions according to embodiments. FIG. 6 intentionally has many similarities with FIG. 3, and much of the description of elements of FIG. 3 applies to corresponding elements of FIG. 6. Functions of the WCD system, such as those described above, can be allocated differently, for instance as second or third functions described below. Plus, they might be renumbered because words like "second" and "third" are mere differentiating labels.

In FIG. 6, a WCD system, which is not indicated separately, has one or more processors 688. Processor(s) 688 are configured to perform a first defibrillation function 611, and at least one second function that is distinct from defibrillation function 611. A set 620 of such possible additional second functions is shown, namely functions 621, 622, although more are possible. Processor(s) 688 are further configured to perform at least one third function, which is distinct from defibrillation function 611 and from the second functions of set 620. In the example of FIG. 6, there is a set 630 of such possible additional third functions, namely functions 631, 632, although more are possible.

The WCD system of FIG. 6 also has an action unit 660 that has a user interface 667. The patient may enter action inputs 668 in user interface 667. Action unit 660 is shown in gray domain 391. Action inputs 668 may affect the functions of set 620, or set 630. More particularly, an aspect of the performance of one of the second functions or one of the third functions can be controlled by received action input 668.

As such, processor(s) 688 may receive an action input 668 and perform second function 621, in which an aspect of the performance of second function 621 can be controlled by received action input 668. Moreover, processor(s) 688 may receive wireless input 618 and subsequently perform again second function 621, in which the same aspect of the subsequent performance of second function 621 can be controlled by received wireless input 618.

The WCD system of FIG. 6 further cooperates with a mobile communication device 610 that has a user interface 617. The patient may enter wireless inputs 618 in user interface 617. Mobile communication device 610 is shown in clear domain 392. Wireless inputs 618 may affect the functions of set 620, but not those of set 630. More particularly, an aspect of the performance of one of the third functions can be controlled by received action input 668, but not by received wireless input 618.

As can be seen, the functions of set 620 can be controlled redundantly, either by action inputs 668, or by wireless inputs 618 of mobile communication device 610. However, the functions of set 630 can be controlled exclusively, by action inputs 668 but not by wireless inputs 618. In this context, the use of the word "exclusively" means the lack of control by one of action unit 660 and mobile communication device 610. In some embodiments, third functions 631, 632 might be further controllable by other means, and so on.

The devices and/or systems mentioned in this document perform functions, processes and/or methods. These functions, processes and/or methods may be implemented by one or more devices that include logic circuitry. Such a device can be alternately called a computer, and so on. It may be a standalone device or computer, such as a general purpose computer, or part of a device that has one or more additional functions. The logic circuitry may include a processor and non-transitory computer-readable storage media, such as memories, of the type described elsewhere in this document. Often, for the sake of convenience only, it is preferred to implement and describe a program as various interconnected distinct software modules or features. These, along with data are individually and also collectively known as software. In some instances, software is combined with hardware, in a mix called firmware.

Moreover, methods and algorithms are described below. These methods and algorithms are not necessarily inherently associated with any particular logic device or other apparatus. Rather, they are advantageously implemented by programs for use by a computing machine, such as a general-purpose computer, a special purpose computer, a microprocessor, a processor such as described elsewhere in this document, a WCD system, and so on.

This detailed description includes flowcharts, display images, algorithms, and symbolic representations of program operations within at least one computer readable medium. An economy is achieved in that a single set of flowcharts is used to describe both programs, and also methods. So, while flowcharts described methods in terms of boxes, they also concurrently describe programs.

Methods are now described.

Figure 7:
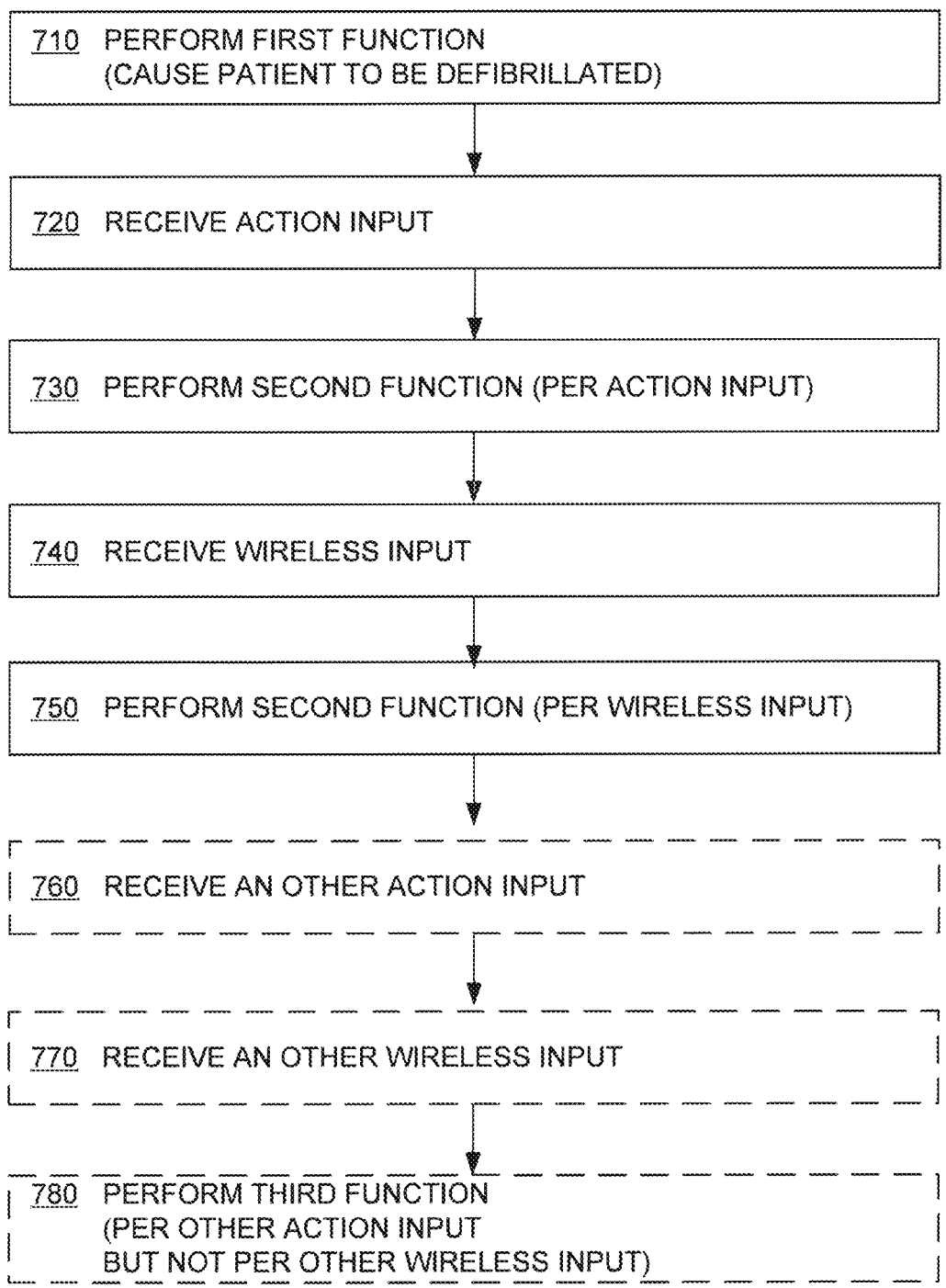
FIG. 7 is a flowchart for illustrating methods according to embodiments.

FIG. 7 shows a flowchart 700 for describing methods according to embodiments. Some functions of a WCD system may be controlled redundantly. For example, according to an operation 710, a first function is performed. The first function may be to cause a patient to be defibrillated, for example by controlling a discharge circuit to discharge a stored electrical charge through the patient, while the patient is wearing a support structure of a WCD system.

According to another operation 720, an action input may be received. According to another operation 730, a second function that is distinct from the first function may be performed. An aspect of the performance of the second function may be controlled by the action input received at operation 720.

According to another operation 740, a wireless input may be received. According to another operation 750, the second function of operation 730 may be subsequently performed again. The aspect of the subsequent performance of the second function that was controlled by the action input of operation 720 may be controlled by the wireless input of operation 740.

Moreover, other functions of the WCD system may optionally be controlled exclusively, meaning not by one of the two functionalities. An example of this was functions of set 630. In such embodiments, according to another, optional operation 760, another action input may be received. According to another, optional operation 770, another wireless input may be received. And according to another, optional operation 780, a third function may be performed. The third function can be distinct from the first and the second functions. An aspect of the performance of the third function can be controlled by the other action input received at operation 760, but not by the other wireless input received at operation 770.

Returning to FIG. 6, as mentioned previously, functions 631, 632 in set 630 are accessible by action unit 660 exclusively. In addition to this, some additional functions may be accessible by the mobile communication device exclusively. Examples are now described.

Figure 8:
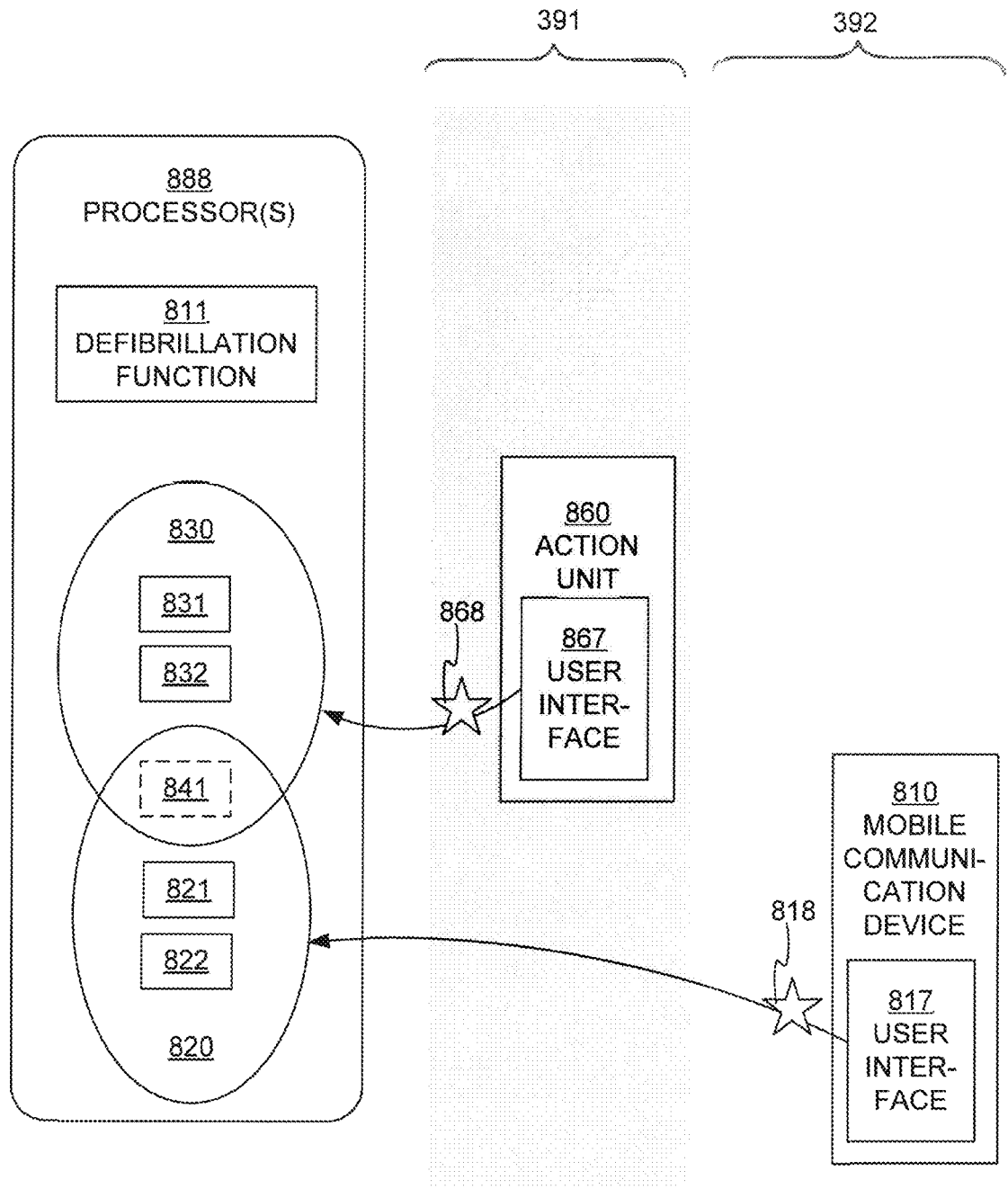
FIG. 8 is a diagram showing a sample allocation of access of functions according to embodiments.

FIG. 8 is a diagram showing a sample allocation of access of functions according to embodiments. FIG. 8 intentionally has many similarities with FIGS. 3 and 6, and much of the description of elements of FIGS. 3 and 6 applies to corresponding elements of FIG. 8. Functions of the WCD system, such as those described above, can be allocated differently, for instance as second or third or fourth functions described below, and can be in different combinations.

In FIG. 8, a WCD system, which is not indicated separately, has one or more processors 888. Processor(s) 888 are configured to perform a first defibrillation function 811, and at least one second function that is distinct from defibrillation function 811. A set 820 of such possible additional second functions is shown, namely functions 821, 822, although more are possible. Processor(s) 888 are further configured to perform at least one third function, which is distinct from defibrillation function 811 and from the second functions of set 820. In the example of FIG. 8, there is a set 830 of such possible additional third functions, namely functions 831, 832, although more are possible. Function 841 is optional, and described later.

The WCD system of FIG. 8 further cooperates with a mobile communication device 810 that has a user interface 817. The patient may enter wireless inputs 818 in user interface 817. Mobile communication device 810 is shown in clear domain 392. Wireless inputs 818 may affect the functions of set 820, but not necessarily those of set 830. More particularly, an aspect of the performance of one of the second functions can be controlled by received wireless input 818, but not necessarily an aspect of the performance of one of the third functions.

The WCD system of FIG. 8 also has an action unit 860 that has a user interface 867. The patient may enter action inputs 868 in user interface 867. Action unit 860 is shown in gray domain 391. Action inputs 868 may affect the functions of set 830, but not necessarily those of set 820. More particularly, an aspect of the performance of one of the third functions can be controlled by received action input 868, but not necessarily an aspect of the performance of one of the second functions.

FIG. 8 shows examples of where processor(s) 888 can be configured to receive one of the action inputs 868, receive one of the wireless inputs 818, and perform a second function 821, in which an aspect of the performance of second function 821 is controlled by the received wireless input but not by the received action input. Processor(s) 888 can further be configured to perform a third function 831, in which an aspect of the performance of the third function is controlled by the received action input but not by the received wireless input.

Moreover, a fourth function 841 can be accessed redundantly. As such, processor(s) 888 may receive an action input 868 and perform fourth function 841, in which an aspect of the performance of fourth function 841 can be controlled by received action input 868. Moreover, processor(s) 888 may receive wireless input 818 and subsequently perform again fourth function 841, in which the same aspect of the subsequent performance of fourth function 841 can be controlled by received wireless input 818.

Figure 9:
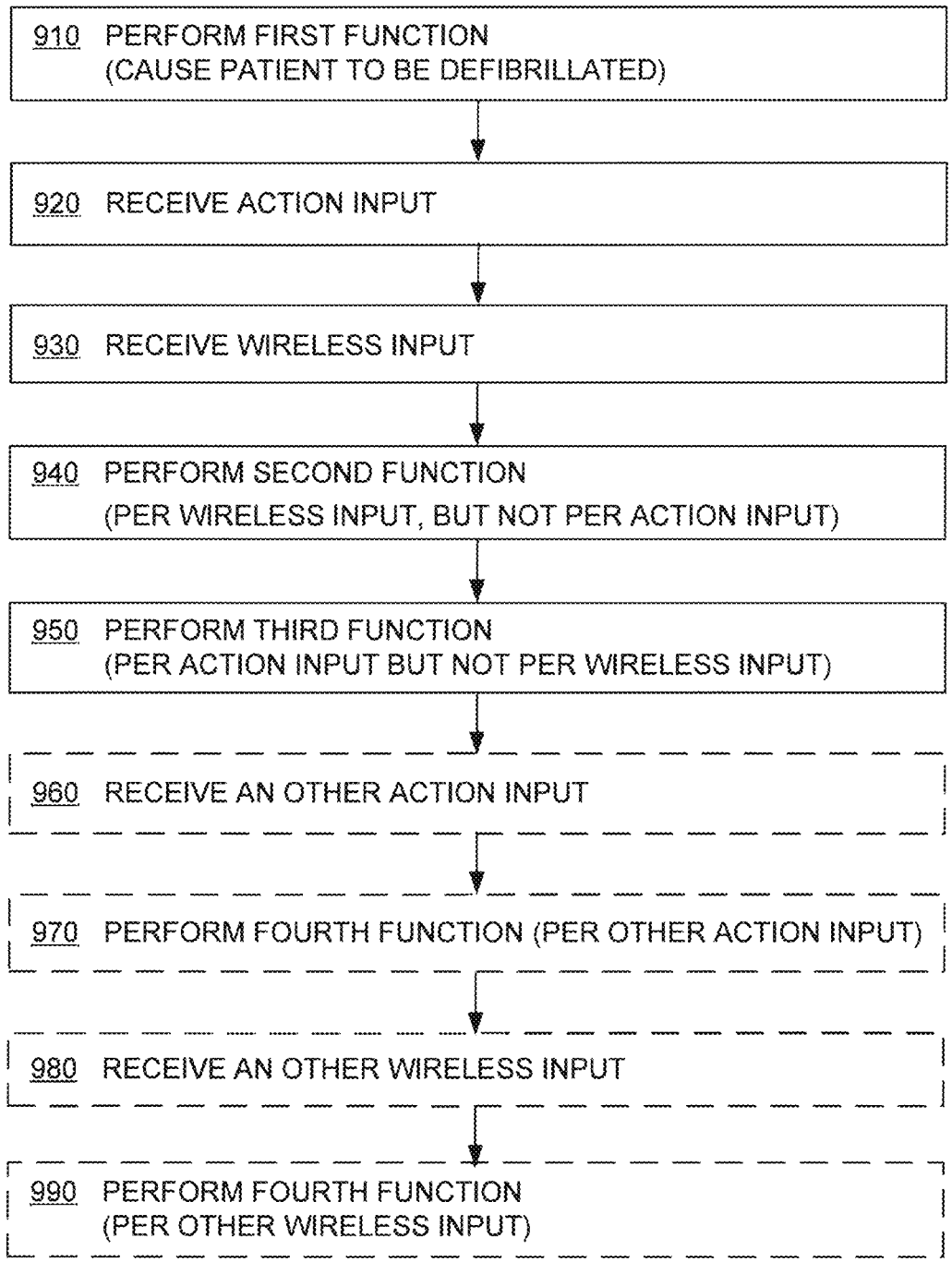
FIG. 9 is a flowchart for illustrating methods according to embodiments.

FIG. 9 shows a flowchart 900 for describing methods according to embodiments. Some functions of a WCD system may be controlled partly mutually exclusively.

According to an operation 910, a first function is performed similarly as was described for operation 710. According to another operation 920, an action input may be received, and according to another operation 930, a wireless input may be received.

According to another operation 940, a second function that is distinct from the first function may be performed. An aspect of the performance of the second function may be controlled by the wireless input received at operation 930, but not by the action input received at operation 920.

According to another operation 950, a third function distinct from the first and the second functions may be performed. An aspect of the performance of the third function may be controlled by the action input received at operation 920, but not by the wireless input received at operation 930.

Moreover, other functions of the WCD system may optionally be controlled redundantly, meaning by either one of the two functionalities. For example, according to another, optional operation 960, another action input may be received. According to another, optional operation 970, a fourth function distinct from the first, the second and the third functions may be performed. An aspect of the performance of the fourth function may be controlled by the other action input received at operation 960. According to another, optional operation 980, another wireless input may be received. According to another, optional operation 990, the fourth function of operation 970 may be subsequently performed again. The aspect of the subsequent performance of the fourth function that was controlled by the action input of operation 960 may be controlled by the other wireless input of operation 980.

In some embodiments, a portion of a WCD system is separable, and carried by the patient instead of being worn. Examples are now described.

Figure 10:
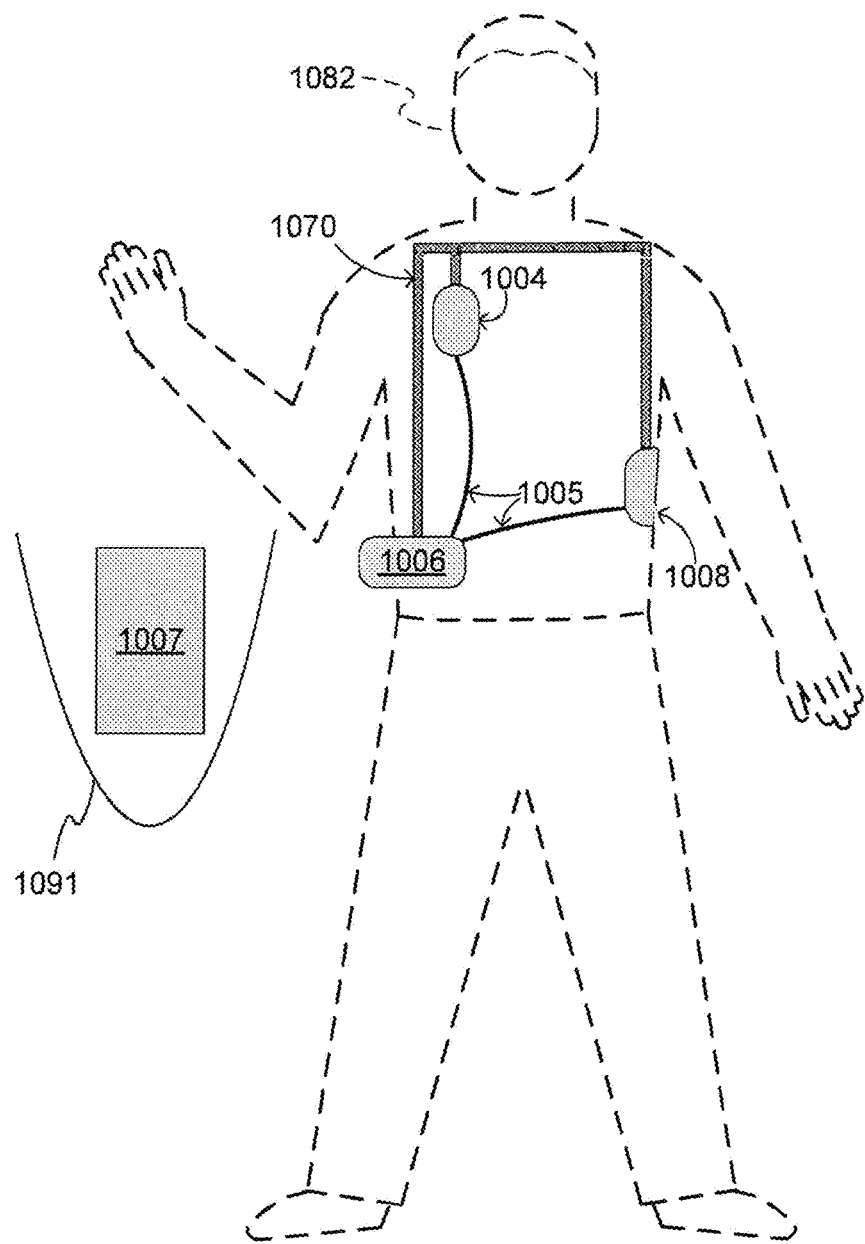
FIG. 10 is a diagram for showing separable embodiments of WCD systems.

Referring to FIG. 10, a patient 1082 is shown, along with components of a WCD system. The components include a support structure 1070 that can be as described for support structure 170. Coupled to support structure 1070 are a component 1006, and electrodes 1004, 1008 that are also electrically coupled to component 1006 with leads 1005.

Another component 1007 cooperates with component 1006, and is carried in container 1091 that can be a suitcase, a handbag, a backpack, and so on. Component 1007 can thus be carried out of sight. Component 1007 maybe coupled by a wire with component 1006, for example both can be electronics modules. In some embodiments, component 1006 is a defibrillator. In some embodiments, component 1007 is an action unit.

Figure 11A:
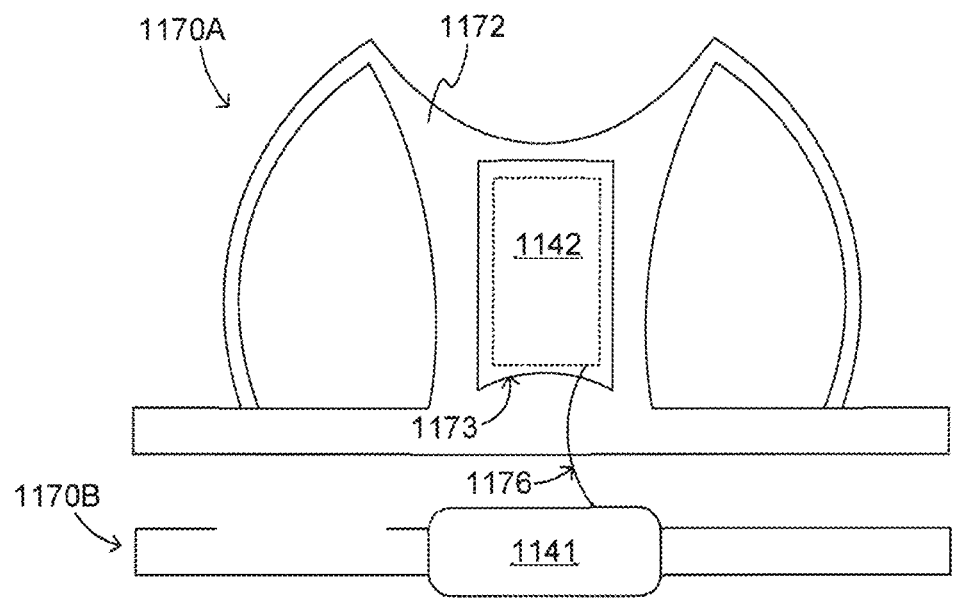
FIG. 11A shows sample components of a WCD system according to embodiments.
Figure 11B:
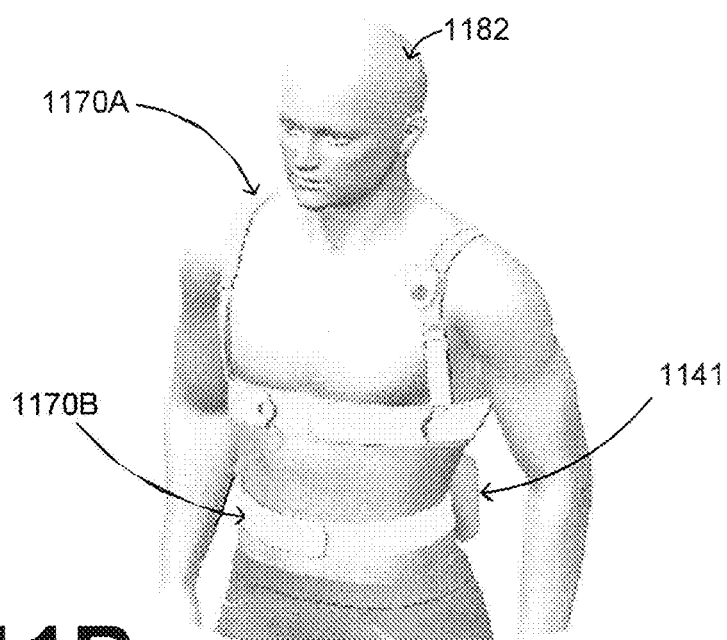
FIG. 11B shows how the components of FIG. 11A may be worn by a patient.

FIG. 11A shows sample components of a WCD system according to embodiments, and FIG. 11B shows how they can be worn by a patient 1182. The components of FIG. 11A include a support structure that has an upper harness 1170A and a lower harness 1170B. The support structure is configured to be worn by patient 1182, in that both upper harness 1170A and lower harness 1170B are configured to be worn—it would be the same if the support structure were made from a single harness, belt, etc.

A first electronics module 1141 is configured to be coupled to the support structure and, more particularly, to lower harness 1170B. The coupling is such that, when the support structure is worn by patient 1182, first electronics module 1141 is substantially at a lumbar region of patient 1182. In some embodiments, first electronics module 1141 includes a power source that is configured to store an electrical charge, as per the above.

The WCD system further includes a second electronics module 1142. Second electronics module 1142 is electrically coupled to first electronics module 1141 via a cable 1176. Second electronics module 1142 may include a discharge circuit, as per the above.

Upper harness 1170A has a main body 1172 with a pocket 1173. Second electronics module 1142 can be provided in pocket 1173.

In the methods described above, each operation can be performed as an affirmative step of doing, or causing to happen, what is written that can take place. Such doing or causing to happen can be by the whole system or device, or just one or more components of it. It will be recognized that the methods and the operations may be implemented in a number of ways, including using systems, devices and implementations described above. In addition, the order of operations is not constrained to what is shown, and different orders may be possible according to different embodiments. Examples of such alternate orderings may include overlapping, interleaved, interrupted, reordered, incremental, preparatory, supplemental, simultaneous, reverse, or other variant orderings, unless context dictates otherwise. Moreover, in certain embodiments, new operations may be added, or individual operations may be modified or deleted. The added operations can be, for example, from what is mentioned while primarily describing a different system, apparatus, device or method.

A person skilled in the art will be able to practice the present invention in view of this description, which is to be taken as a whole. Details have been included to provide a thorough understanding. In other instances, well-known aspects have not been described, in order to not obscure unnecessarily this description. Plus, any reference to any prior art in this description is not, and should not be taken as, an acknowledgement or any form of suggestion that such prior art forms parts of the common general knowledge in any country or any art.

This description includes one or more examples, but this fact does not limit how the invention may be practiced. Indeed, examples, instances, versions or embodiments of the invention may be practiced according to what is described, or yet differently, and also in conjunction with other present or future technologies. Other such embodiments include combinations and sub-combinations of features described herein, including for example, embodiments that are equivalent to the following: providing or applying a feature in a different order than in a described embodiment; extracting an individual feature from one embodiment and inserting such feature into another embodiment; removing one or more features from an embodiment; or both removing a feature from an embodiment and adding a feature extracted from another embodiment, while providing the features incorporated in such combinations and sub-combinations.

In this document, the phrases "constructed to" and/or "configured to" denote one or more actual states of construction and/or configuration that is fundamentally tied to physical characteristics of the element or feature preceding these phrases and, as such, reach well beyond merely describing an intended use. Any such elements or features can be implemented in a number of ways, as will be apparent to a person skilled in the art after reviewing the present disclosure, beyond any examples shown in this document.

Any and all parent, grandparent, great-grandparent, etc. patent applications, whether mentioned in this document or in an Application Data Sheet (ADS) of this patent application, are hereby incorporated by reference herein, including any priority claims made in those applications and any material incorporated by reference, to the extent such subject matter is not inconsistent herewith.

In this description a single reference numeral may be used consistently to denote a single aspect, component, or process. Moreover, a further effort may have been made in the drafting of this description to choose similar though not identical reference numerals to denote versions or embodiments of an aspect, component or process that are the same or possibly different. Where made, such a further effort was not required, but was nevertheless made gratuitously to accelerate comprehension by the reader. Even where made in this document, such an effort might not have been made completely consistently throughout the many versions or embodiments that are made possible by this description. Accordingly, the description controls. Any similarity in reference numerals may be used to confirm a similarity in the text, or even possibly a similarity where express text is absent, but not to confuse aspects where the text or the context indicates otherwise.

The claims of this document define certain combinations and subcombinations of elements, features and steps or operations, which are regarded as novel and non-obvious. Additional claims for other such combinations and subcombinations may be presented in this or a related document. These claims are intended to encompass within their scope all changes and modifications that are within the true spirit and scope of the subject matter described herein. The terms used herein, including in the claims, are generally intended as "open" terms. For example, the term "including" should be interpreted as "including but not limited to," the term "having" should be interpreted as "having at least," etc. If a specific number is ascribed to a claim recitation, this number is a minimum but not a maximum unless stated otherwise. For example, where a claim recites "a" component or "an" item, it means that it can have one or more of this component or item.

What is claimed is:

1. A wearable medical device system, comprising:
    a support structure configured to be worn by a patient;
    an energy storage device configured to store an electrical charge;
    a discharge circuit coupled to the energy storage device;
    a plurality of electrodes coupled to the support structure and the discharge circuit, the plurality of electrodes configured to sense electrocardiogram (ECG) signals and to provide an electrical charge to the patient from the energy storage device via the discharge circuit;
    a communication module configured to be coupled to the support structure and to establish a local communication link with a hand-held mobile device comprising a smartphone; and
    one or more processors coupled to the discharge circuit and the communication module, wherein while the patient is wearing the support structure, the one or more processors are configured to:
        determine using sensed ECG signals whether the patient has a shockable arrhythmia,
        responsive to a determination that the patient has a shockable arrhythmia, control the discharge circuit to discharge stored electrical charge through at least a subset of the plurality of electrodes, and
        transmit a defibrillation status of the patient to the mobile device and a command to the mobile device to cause the defibrillation status and a location of the patient to be provided to a remote device via the mobile device, wherein the remote device is located at a remote assistance center, an Emergency Medical Service (EMS) facility, or a remote party.

2. The wearable medical device system of claim 1, wherein the wearable medical device system includes a location sensor to determine the location of the patient, and the one or more processors are configured to transmit the location of the patient, determined by the location sensor of the wearable medical device, to the remote device via the mobile device.

3. The wearable medical device system of claim 1, wherein the mobile device includes a location sensor to determine the location of the patient, and the one or more processors are configured to cause the mobile device to transmit the location of the patient, determined by the location sensor of the mobile device, to the remote device.

4. The wearable medical device system of claim 1, wherein the remote device is located at the Emergency Medical Service (EMS) facility.

5. The wearable medical device system of claim 1, wherein the one or more processors are configured to send a command to the remote device to transmit the location of the patient to the Emergency Medical Service (EMS) facility when the remote device is not located at the EMS facility.

6. The wearable medical device system of claim 1, wherein the one or more processors are configured to send a command to the remote device to transmit the defibrillation status of the patient to the Emergency Medical Service (EMS) facility when the remote device is at a location other than the EMS facility.

7. The wearable medical device system of claim 1, wherein the one or more processors are configured to transmit a defibrillation status of the patient to the remote device via the mobile device.

8. The wearable medical device system of claim 1, wherein the one or more processors are configured to transmit a defibrillation status of the patient to the mobile device to enable the patient to provide the defibrillation status to the Emergency Medical Service (EMS facility when the remote device is at a location other than the EMS facility.

9. A wearable medical device system, comprising:
a support structure configured to be worn by a patient;
an energy storage device configured to store an electrical charge;
a discharge circuit coupled to the energy storage device;
a plurality of electrodes coupled to the support structure and the discharge circuit, the plurality of electrodes configured to sense electrocardiogram (ECG) signals and/or to provide an electrical charge to the patient from the energy storage device via the discharge circuit;
a remote device, wherein the remote device is located at a remote assistance center, an Emergency Medical Service (EMS) facility, or a remote party;
a communication module configured to be coupled to the support structure and to establish a local communication link with a hand-held mobile device comprising a smartphone; and
one or more processors coupled to the discharge circuit and the communication module, wherein while the patient is wearing the support structure, the one or more processors are configured to:
determine using sensed ECG signals whether the patient has a shockable arrhythmia,
responsive to a determination that the patient has a shockable arrhythmia, control the discharge circuit to discharge stored electrical charge through at least a subset of the plurality of electrodes, and
send a command to the mobile device to send to the remote device information indicative of the patient being defibrillated and the location of the patient and/or the mobile device,
wherein a user of the remote device is enabled to provide the information to an emergency service of the patient's location and defibrillation status.

10. The wearable medical device system of claim 9, wherein the wearable medical device system includes a location sensor to determine the location of the patient, and the one or more processors are configured to transmit the location of the patient, determined by the location sensor of the wearable medical device, to the remote device via the mobile device.

11. The wearable medical device system of claim 10, wherein the mobile device includes a location sensor to determine the location of the patient, and the one or more processors are configured to cause the mobile device to transmit the location of the patient, determined by the location sensor of the mobile device, to the remote device.

12. The wearable medical device system of claim 10, wherein the remote device is located at the Emergency Medical Service (EMS) facility.

13. The wearable medical device system of claim 10, wherein the one or more processors are configured to send a command to the remote device to transmit the location of the patient to the Emergency Medical Service (EMS) facility when the remote device is at a location other than the EMS facility.

14. The wearable medical device system of claim 10, wherein the one or more processors are configured to send a command to the remote device to transmit the defibrillation status of the patient to an Emergency Medical Service (EMS) facility when the remote device is at a location other than the EMS facility.

15. The wearable medical device system of claim 10, wherein the one or more processors are configured to transmit a defibrillation status of the patient to the remote device via the mobile device.

16. A method to operate a wearable medical device system, the method comprising:
determining using sensed electrocardiogram (ECG) signals whether a patient wearing the wearable medical device system has a shockable arrhythmia,
controlling a discharge circuit of the wearable medical device system to discharge stored electrical charge through a plurality of electrodes responsive to a determination that the patient has a shockable arrhythmia, and
transmitting a defibrillation status of the patient to a hand-held mobile device comprising a smartphone, and a command to the mobile device to cause the defibrillation status and a location of the patient to be provided to a remote device via the mobile device, wherein the remote device is located at a remote assistance center, an Emergency Medical Service (EMS) facility, or a remote party.

17. The method of claim 16, further comprising determining the location of the patient using a location sensor in the wearable medical device system, and transmitting the location of the patient to the mobile device.

18. The method of claim 16, further comprising determining the location of the patient using a location sensor in the mobile device.

19. The method of claim 16, wherein the remote device is located at an Emergency Medical Service (EMS) facility.

20. The method of claim 16, further comprising causing the remote device to transmit the location of the patient to the Emergency Medical Service (EMS) facility when the remote device is at a location other than the EMS facility.

* * * * *

UNITED STATES PATENT AND TRADEMARK OFFICE
CERTIFICATE OF CORRECTION

PATENT NO. : 11,376,425 B2
APPLICATION NO. : 16/678727
DATED : July 5, 2022
INVENTOR(S) : Finch et al.

Page 1 of 1

It is certified that error appears in the above-identified patent and that said Letters Patent is hereby corrected as shown below:

On the Title Page

On page 2, Column 1, Line 1, item (60) Related U.S. Application Data, please delete "Provisional application No. 61/000,404," and replace with -- Provisional application No. 62/000,404, --.

Signed and Sealed this
Twenty-fifth Day of March, 2025

Coke Morgan Stewart
*Acting Director of the United States Patent and Trademark Office*